United States Patent
Tanaka et al.

(10) Patent No.: US 11,053,960 B2
(45) Date of Patent: Jul. 6, 2021

(54) HYDRAULIC FORCEPS SYSTEM

(71) Applicant: KAWASAKI JUKOGYO KABUSHIKI KAISHA, Kobe (JP)

(72) Inventors: Hideki Tanaka, Nishinomiya (JP); Mariko Ogata, Kobe (JP); Hiroaki Fujimoto, Kobe (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 253 days.

(21) Appl. No.: 16/474,428

(22) PCT Filed: Dec. 20, 2017

(86) PCT No.: PCT/JP2017/045657
§ 371 (c)(1),
(2) Date: Jun. 27, 2019

(87) PCT Pub. No.: WO2018/123753
PCT Pub. Date: Jul. 5, 2018

(65) Prior Publication Data
US 2019/0345959 A1    Nov. 14, 2019

(30) Foreign Application Priority Data
Dec. 27, 2016 (JP) .............................. JP2016-252568

(51) Int. Cl.
*F15B 15/04* (2006.01)
*A61B 17/28* (2006.01)
(Continued)

(52) U.S. Cl.
CPC .............. *F15B 15/04* (2013.01); *A61B 17/28* (2013.01); *A61B 34/37* (2016.02); *A61B 2017/00539* (2013.01); *F15B 2215/30* (2013.01)

(58) Field of Classification Search
CPC .. F15B 15/04; F15B 2215/30; F15B 15/2838; F15B 2211/633; F15B 2211/6651;
(Continued)

(56) References Cited
U.S. PATENT DOCUMENTS 5,431,645 A 7/1995 Smith et al.
5,791,231 A * 8/1998 Cohn ....................... B25J 9/144
606/1
(Continued)

FOREIGN PATENT DOCUMENTS

| CN | 201614281 U | 10/2010 |
|---|---|---|
| JP | 2013-220273 A | 10/2013 |
| WO | 2011/094269 A2 | 8/2011 |

*Primary Examiner* — Julian W Woo
(74) *Attorney, Agent, or Firm* — Oliff PLC

(57) ABSTRACT

A hydraulic forceps system includes: robotic forceps including: a gripper, first piston coupled to the gripper, first cylinder forming first pressure chamber, filled with a hydraulic fluid, together with the first piston, second piston, second cylinder forming a second pressure chamber, filled with hydraulic fluid, together with the second piston, communication passage through which the chambers communicate, motor that drives the second piston via a linear motion mechanism; control device that controls the motor based on a command position for the first piston; and position sensor used for detecting a position of the second piston. The control device includes: an observer that derives an estimated position of the first piston based on the position of the second detected by the sensor; and a position controller that derives a target rotational speed of the motor based on a deviation between the estimated position of the first piston and the command position.

6 Claims, 3 Drawing Sheets

(51) Int. Cl.
*A61B 34/37* (2016.01)
*A61B 17/00* (2006.01)
(58) Field of Classification Search
CPC .... F15B 2211/20515; F15B 2211/7052; F15B 2211/7653; F15B 7/08; A61B 34/37; A61B 17/28; A61B 2017/00539; A61B 17/29; A61B 34/35; B25J 15/0206; B25J 9/144
See application file for complete search history.

(56) References Cited

U.S. PATENT DOCUMENTS

| | | | |
|---|---|---|---|
| 7,988,215 B2 * | 8/2011 | Seibold | F15B 15/10 294/213 |
| 2006/0235368 A1 * | 10/2006 | Oz | A61B 17/29 606/1 |
| 2013/0172812 A1 | 7/2013 | Kirschenman | |

* cited by examiner $$X = \begin{bmatrix} x_1 \\ x_2 \\ \dot{x}_1 \\ \dot{x}_2 \\ P \end{bmatrix} \quad \dot{X} = \begin{bmatrix} \dot{x}_1 \\ \dot{x}_2 \\ \ddot{x}_1 \\ \ddot{x}_2 \\ \dot{P} \end{bmatrix} \quad Y = \begin{bmatrix} x_2 \\ P \end{bmatrix}$$

HYDRAULIC FORCEPS SYSTEM

TECHNICAL FIELD

The present invention relates to a hydraulic forceps system including robotic forceps whose gripper is opened and closed by utilizing hydraulic pressure.

BACKGROUND ART

Conventionally, wire-driven robotic forceps are used in a surgery assisting robot. The gripper of the robotic forceps is opened/closed by pulling/retracting a wire. In recent years, robotic forceps whose gripper is opened and closed by utilizing pneumatic pressure have been proposed to replace wire-driven robotic forceps. For example, FIG. 9 of Patent Literature 1 shows a pneumatic actuator used in such robotic forceps. FIG. 4 shows this pneumatic actuator 100.

Specifically, in the pneumatic actuator 100, a piston 130 is accommodated in a cylinder 140. The piston 130 is coupled to a gripper 110 by a rod 120. The cylinder 140 is provided with a displacement sensor 150, which detects a moving amount of the piston 130. The displacement sensor 150 is used for calculating an external force F.

CITATION LIST

Patent Literature

PTL 1: Japanese Laid-Open Patent Application Publication No. 2013-220273

SUMMARY OF INVENTION

Technical Problem

In the pneumatic actuator 100 shown in FIG. 4, in order to control the opening and closing of the gripper 110, the displacement sensor 150 can be used also as a position sensor for detecting the position of the piston 130. However, since the distal end portions of the robotic forceps are very thin, it is difficult to install such a position sensor (displacement sensor 150) at the distal end portions of the robotic forceps.

In view of the above, an object of the present invention is to make it possible to control the opening and closing of the gripper without installing the position sensor at the distal end portions of the robotic forceps.

Solution to Problem

In order to solve the above-described problems, the present invention provides a hydraulic forceps system including: robotic forceps including a gripper, a first piston coupled to the gripper, a first cylinder accommodating the first piston and forming a first pressure chamber together with the first piston, the first pressure chamber being filled with a hydraulic fluid, a second piston, a second cylinder accommodating the second piston and forming a second pressure chamber together with the second piston, the second pressure chamber being filled with the hydraulic fluid, a communication passage through which the first pressure chamber and the second pressure chamber communicate with each other, and a motor that drives the second piston via a linear motion mechanism; a position sensor used for detecting a position of the second piston; and a control device that controls the motor based on a command position for the first piston. The control device includes: an observer that derives an estimated position of the first piston based on the position of the second piston detected by using the position sensor; and a position controller that derives a target rotational speed of the motor based on a deviation between the estimated position of the first piston and the command position.

According to the above configuration, since the incompressible hydraulic fluid is used, the moving amount of the first piston coupled to the gripper, i.e., the moving amount of the first piston disposed at the distal end side of the robotic forceps, is proportional to the moving amount of the second piston, almost without being affected by the external force. In addition, the second piston is driven by the motor via the linear motion mechanism. Accordingly, by controlling the motor with the control device based on the command position for the first piston, the opening and closing of the gripper can be controlled. Moreover, the control device includes the observer, which derives the estimated position of the first piston based on the position of the second piston, and the estimated position of the first piston is compared with the command position. Therefore, installation of a position sensor that detects the position of the first piston is unnecessary. That is, the control of the opening and closing of the gripper is made possible without installing the position sensor at the distal end portions of the robotic forceps.

For example, the position sensor may be a rotary encoder that detects a rotational displacement of the motor and converts the rotational displacement into the position of the second piston.

The above hydraulic forceps system may further include a pressure sensor that detects a pressure of the hydraulic fluid. The observer may derive the estimated position of the first piston based on the pressure of the hydraulic fluid detected by the pressure sensor and the position of the second piston detected by using the position sensor. According to this configuration, the precision of the estimation of the position of the first piston can be improved compared to a case where the estimated position of the first piston is derived based solely on the position of the second piston.

For example, the observer may: derive an estimated position of the second piston and an estimated pressure of the hydraulic fluid; calculate an estimated error based on a deviation between the pressure of the hydraulic fluid detected by the pressure sensor and the estimated pressure of the hydraulic fluid and a deviation between the position of the second piston detected by using the position sensor and the estimated position of the second piston; and feed back the calculated estimated error to the deriving of the estimated position of the first piston.

Advantageous Effects of Invention

The present invention makes it possible to control the opening and closing of the gripper without installing the position sensor at the distal ends of the robotic forceps.

DESCRIPTION OF EMBODIMENTS

Figure 1:
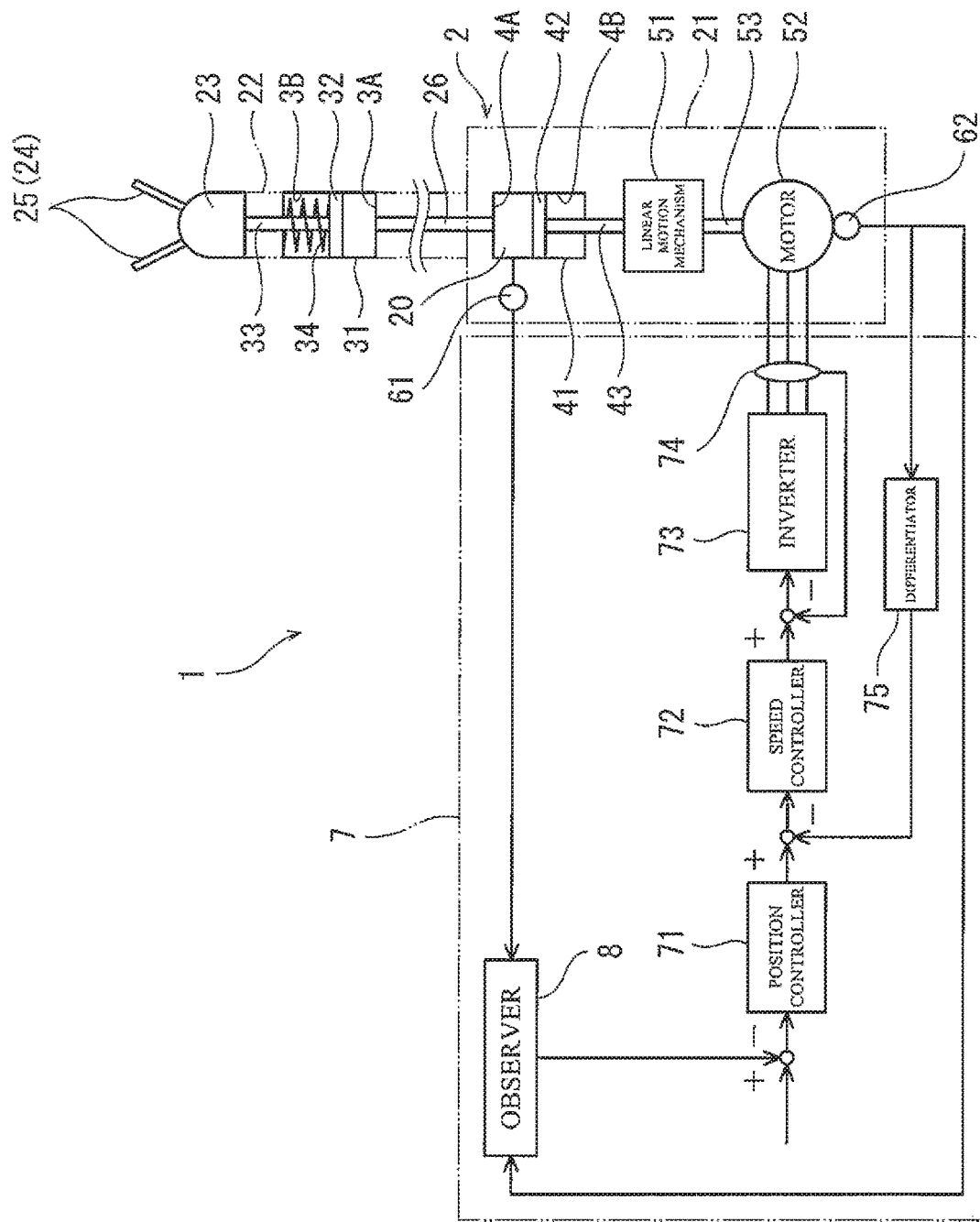
FIG. 1 shows a schematic configuration of a hydraulic forceps system according to one embodiment of the present invention.

FIG. 1 shows a hydraulic forceps system 1 according to one embodiment of the present invention. The hydraulic forceps system 1 includes robotic forceps 2 and a control device 7.

For example, in a case where the hydraulic forceps system 1 is used in a surgery assisting robot, a doctor operates the robotic forceps 2 by remote control using a master device, while the robotic forceps 2 are attached to a slave device. In this case, the control device 7 may be mounted in the master device or in the slave device. Alternatively, the control device 7 may be incorporated in a drive unit 21 of the robotic forceps 2. The drive unit 21 will be described below.

The robotic forceps 2 include a gripper 24, which is opened and closed by utilizing the hydraulic pressure of a hydraulic fluid 20. The hydraulic fluid 20 is not limited to a particular type of fluid, but may be a saline solution or oil, for example.

Specifically, the robotic forceps 2 include: the drive unit 21; an insertion shaft 22 extending from the drive unit 21 and inserted in the body of a patient; and the gripper 24 provided at the distal end of the insertion shaft 22 and formed by a pair of tips 25. Although not illustrated, a mechanism that slides the insertion shaft 22 in its axial direction, and a mechanism that rotates the insertion shaft 22 about its central axis, may be incorporated in the drive unit 21. The insertion shaft 22 may be configured such that the distal end portion thereof is swingable, and a mechanism that swings the distal end portion of the insertion shaft 22 may be incorporated in the drive unit 21.

In the present embodiment, the insertion shaft 22 is a straight tube with high rigidity. However, as an alternative, the insertion shaft 22 may be a flexible tube.

A first cylinder 31 is disposed in the distal end portion of the insertion shaft 22. In the present embodiment, the central axis of the first cylinder 31 coincides with the central axis of the insertion shaft 22. The first cylinder 31 includes: a tubular portion; a front wall that blocks the inside of the tubular portion from the gripper 24 side; and a rear wall that blocks the inside of the tubular portion from the side opposite to the gripper 24 side.

A first piston 32 is accommodated in the first cylinder 31. A first pressure chamber 3A is formed between the first piston 32 and the rear wall of the first cylinder 31, and a back pressure chamber 3B is formed between the first piston 32 and the front wall of the first cylinder 31. The inside of the first pressure chamber 3A is filled with the hydraulic fluid 20, and the inside of the back pressure chamber 3B is open to the atmosphere. In the present embodiment, a spring 34, which urges the first piston 32, is disposed in the back pressure chamber 3B.

The first piston 32 is coupled to the gripper 24 by a rod 33 via a link mechanism 23. The rod 33 penetrates the front wall of the first cylinder 31. The link mechanism 23 converts linear motion of the rod 33 into opening/closing motion of the gripper 24.

A second cylinder 41, which is connected to the first cylinder 31 by a communication passage 26, is disposed in the drive unit 21. In the present embodiment, the axial direction of the second cylinder 41 is parallel to the axial direction of the insertion shaft 22. However, the axial direction of the second cylinder 41 is not particularly limited. The second cylinder 41 includes: a tubular portion; a front wall that blocks the inside of the tubular portion from the insertion shaft 22 side; and a rear wall that blocks the inside of the tubular portion from the side opposite to the insertion shaft 22 side.

A second piston 42 is accommodated in the second cylinder 41. A second pressure chamber 4A is formed between the second piston 42 and the front wall of the second cylinder 41, and a back pressure chamber 4B is formed between the second piston 42 and the rear wall of the second cylinder 41. The inside of the second pressure chamber 4A is filled with the hydraulic fluid 20, and the inside of the back pressure chamber 4B is open to the atmosphere.

The aforementioned communication passage 26 extends through the inside of the insertion shaft 22, and the first pressure chamber 3A and the second pressure chamber 4A communicate with each other through the communication passage 26. The inside of the communication passage 26 is also filled with the hydraulic fluid 20. For example, the communication passage 26 is formed by a metal tube or a flexible resin tube.

The second piston 42 is coupled to a linear motion mechanism 51 by a rod 43, which penetrates the rear wall of the second cylinder 41. The linear motion mechanism 51 is coupled also to an output shaft 53 of a motor 52. The linear motion mechanism 51 converts rotational motion of the output shaft 53 of the motor 52 into linear motion of the rod 43. That is, the motor 52 drives the second piston 42 via the linear motion mechanism 51 and the rod 43. The motor 52 is, for example, a servomotor.

When the second piston 42 moves forward as a result of the motor 52 rotating in one direction, the hydraulic fluid 20 is supplied from the second pressure chamber 4A to the first pressure chamber 3A, and thereby the first piston 32 moves forward against the urging force of the spring 34. On the other hand, when the second piston 42 moves rearward as a result of the motor 52 rotating in the reverse direction, the urging force of the spring 34 causes the first piston 32 to move rearward, and thereby the hydraulic fluid 20 is discharged from the first pressure chamber 3A to the second pressure chamber 4A. That is, the second cylinder 41, the second piston 42, the linear motion mechanism 51, and the motor 52 form a hydraulic fluid supply/discharge mechanism that supplies and discharges the hydraulic fluid to and from the first pressure chamber 3A.

The control device 7 receives, for example, an input of a command position $tx_1$ for the first piston 32 from the aforementioned master device. Alternatively, the control device 7 may receive an input of an opening degree command for the gripper 24, and the control device 7 may include a command position calculator that calculates the command position $tx_1$ for the first piston 32 based on the opening degree command.

The control device 7 controls the motor 52 based on the command position $tx_1$ for the first piston 32. The control device 7 includes, for example, a CPU and memories such as a ROM and RAM. The CPU executes a program stored in the ROM. Specifically, the control device 7 includes a position controller 71, a speed controller 72, an inverter 73, a differentiator 75, and an observer 8. The control device 7 may be a single device, or may be divided into a plurality of devices.

In the present embodiment, the control device 7 is electrically connected to a pressure sensor 61 and a position sensor 62. The pressure sensor 61 detects the pressure P of the hydraulic fluid 20. The position sensor 62 is used for detecting the position $x_2$ of the second piston 42.

In the present embodiment, the position sensor 62 is a rotary encoder provided on the motor 52. The position sensor 62 detects the rotational displacement of the motor 52, and converts the rotational displacement into the position $x_2$ of the second piston 42. Alternatively, the position sensor 62 may be a linear encoder provided on the linear motion mechanism 51. Further alternatively, the position sensor 62 may be provided on the second cylinder 41, and may directly detect the position $x_2$ of the second piston 42.

The observer 8 derives an estimated position $ex_1$ of the first piston 32 based on the pressure P of the hydraulic fluid 20 detected by the pressure sensor 61 and the position $x_2$ of the second piston 42 detected by using the position sensor 62. It should be noted that the function of the observer 8 will be described below in detail.

The position controller 71 derives a target rotational speed Vt of the motor 52 based on a deviation $\Delta x_1$ $(=tx_1-ex_1)$ between the estimated position $ex_1$ of the first piston 32 and the command position $tx_1$ for the first piston 32. The relationship between the deviation $\Delta x_1$ and the target rotational speed Vt is preset.

The differentiator 75 calculates the current rotational speed V of the motor 52 by performing differentiation on the position $x_2$ of the second piston 42, which is detected by using the position sensor 62. The speed controller 72 derives a target electric current Ct of the motor 52 based on a deviation $\Delta V$ $(=Vt-V)$ between the target rotational speed Vt and the current rotational speed V of the motor 52. The relationship between the deviation $\Delta V$ and the target electric current Ct is preset.

A current sensor 74 is provided on an electric power line between the inverter 73 and the motor 52. The inverter 73 supplies an electric current to the motor 52, such that a deviation between an electric current Cn detected by the current sensor 74 and the target electric current Ct is small.

Next, the function of the observer 8 is described in detail with reference to FIG. 2. The observer 8 is the modeling of a moving amount of the second piston 42 and a moving amount of the first piston 32 when a force F is applied to the second piston 42. The observer 8 can be represented by a state equation 1 and an output equation 2 shown below. It should be noted that, in the description below, a dot symbol that should be placed above a parameter according to Newton's notation is placed on the upper right of the parameter.

$$X\dot{} =AX+BF \quad (1)$$

$$Y=CX \quad (2)$$

Figures 2, 3:
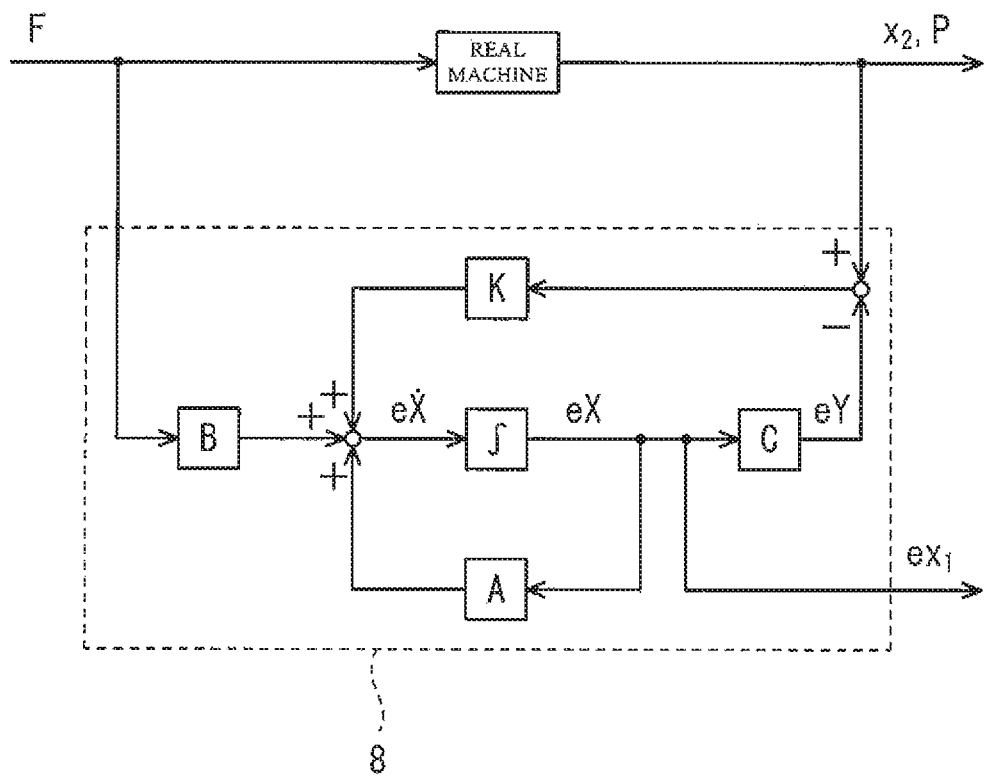
FIG. 2 is a block diagram of an observer.
FIG. 3 shows matrixes representing state parameters.
Figure 4:
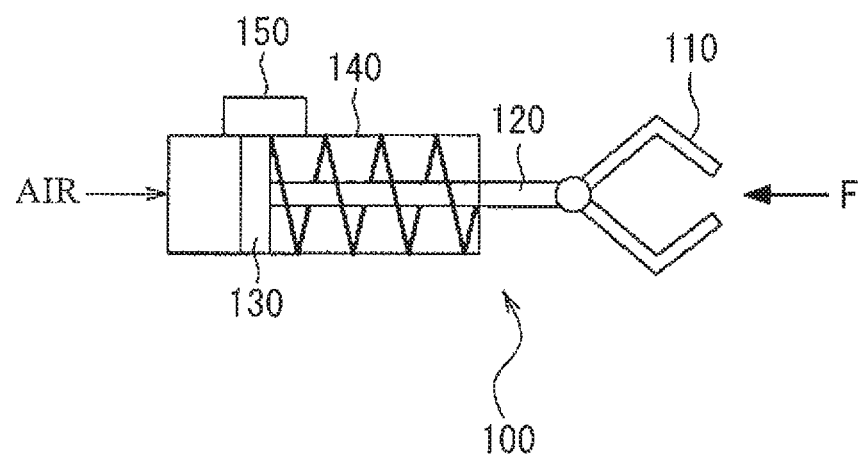
FIG. 4 shows a schematic configuration of a conventional pneumatic actuator used in robotic forceps.

$X\dot{}$, X, Y: state parameters represented by matrixes shown in FIG. 3
  $x_1$: position of the first piston
  $x_2$: position of the second piston
  P: pressure of the hydraulic fluid
  F: force applied to the second piston
  A, B: matrixes each representing a coefficient in the state equation 1
  C: matrix representing a coefficient in the output equation 2

The matrixes A and B are obtained from, for example, a state equation relating to the first piston 32 and a state equation relating to the second piston 42.

To be more specific, the observer 8 first uses the matrixes A and B to obtain an estimated state parameter $eX\dot{}$, and then integrates the estimated state parameter $eX\dot{}$ to calculate an estimated state parameter $X\dot{}$. That is, the observer 8 derives not only the estimated position $ex_1$ of the first piston 32, but also an estimated position $ex_2$ of the second piston 42 and an estimated pressure eP of the hydraulic fluid 20. The derived estimated position $ex_1$ of the first piston 32 is, as mentioned above, compared with the command position $tx_1$ for the first piston 32.

Further, the observer 8 uses the matrix C to extract the estimated position $ex_2$ of the second piston 42 and the estimated pressure eP of the hydraulic fluid 20, and compares them with the position $x_2$ of the second piston 42 detected by using the position sensor 62 and the pressure P of the hydraulic fluid 20 detected by the pressure sensor 61. Then, the observer 8 uses a matrix K to calculate estimated errors for all the elements of the state parameter $X\dot{}$ based on a deviation $\Delta x_2$ $(=x_2-ex_2)$ between the detected position $x_2$ and the estimated position $ex_2$ of the second piston 42 and a deviation $\Delta P$ $(=P-eP)$ between the detected pressure P and the estimated pressure eP of the hydraulic fluid 20. Thereafter, the observer 8 feeds back the calculated estimated errors to the calculation of the estimated state parameter $eX\dot{}$. In other words, the estimated errors are fed back to the deriving of the estimated position $ex_1$ of the first piston 32.

As described above, in the hydraulic forceps system 1 of the present embodiment, since the incompressible hydraulic fluid 20 is used, the moving amount of the first piston 32 coupled to the gripper 24, i.e., the moving amount of the first piston 32 disposed at the distal end side of the robotic forceps 2, is proportional to the moving amount of the second piston 42, almost without being affected by the external force. In addition, the second piston 42 is driven by the motor 52 via the linear motion mechanism 51. Accordingly, by controlling the motor 52 with the control device 7 based on the command position $tx_1$ for the first piston 32, the opening and closing of the gripper 24 can be controlled. Moreover, the control device 7 includes the observer 8, which derives the estimated position $ex_1$ of the first piston 32 based on the position $x_2$ of the second piston 42, and the estimated position $ex_1$ of the first piston 32 is compared with the command position $tx_1$. Therefore, installation of a position sensor that detects the position of the first piston 32 is unnecessary. That is, the control of the opening and closing of the gripper 24 is made possible without installing the position sensor at the distal end portions of the robotic forceps 2.

(Variations)

The present invention is not limited to the above-described embodiment. Various modifications can be made without departing from the spirit of the present invention.

As one example, the pressure sensor 61 may be eliminated, and the observer 8 may derive the estimated position $ex_1$ of the first piston 32 based solely on the position $x_2$ of the second piston 42 detected by using the position sensor 62. However, if the estimated position $ex_1$ of the first piston 32 is derived based on the position $x_2$ of the second piston 42 detected by using the position sensor 62 and the pressure P of the hydraulic fluid 20 detected by the pressure sensor 61 as in the above-described embodiment, the precision of the estimation of the position of the first piston 32 can be improved compared to a case where the estimated position $ex_1$ of the first piston 32 is derived based solely on the position $x_2$ of the second piston 42.

In the above-described embodiment, the first piston 32 is moved rearward by the urging force of the spring 34. However, as an alternative, another hydraulic fluid supply/discharge mechanism including the second cylinder 41, the second piston 42, the linear motion mechanism 51, and the motor 52 may be installed; the second pressure chamber 4A of this other hydraulic fluid supply/discharge mechanism may be connected to the back pressure chamber 3B formed between the front wall of the first cylinder 31 and the first piston 32; and the first piston 32 may be moved rearward by the hydraulic pressure of the hydraulic fluid supplied to the back pressure chamber 3B. As another alternative, one end of a wire may be fixed to the first piston 32, and the first piston 32 may be moved rearward by pulling the wire.

As another example, there may be additionally provided means that make it possible to perform correction on the observer 8 in accordance with the state of the first piston 32 and/or the second piston 42, load conditions, individual differences of the robotic forceps 2, surrounding environment, etc.

REFERENCE SIGNS LIST 1 hydraulic forceps system
2 robotic forceps
20 hydraulic fluid
24 gripper
26 communication passage
31 first cylinder
32 first piston
3A first pressure chamber
41 second cylinder
42 second piston
4A second pressure chamber
51 linear motion mechanism
52 motor
61 pressure sensor
62 position sensor
7 control device
8 observer

The invention claimed is:

1. A hydraulic forceps system comprising:
robotic forceps including a gripper, a first piston coupled to the gripper, a first cylinder accommodating the first piston and forming a first pressure chamber together with the first piston, the first pressure chamber being filled with a hydraulic fluid, a second piston, a second cylinder accommodating the second piston and forming a second pressure chamber together with the second piston, the second pressure chamber being filled with the hydraulic fluid, a communication passage through which the first pressure chamber and the second pressure chamber communicate with each other, and a motor that drives the second piston via a linear motion mechanism;
a position sensor used for detecting a position of the second piston; and
a control device that controls the motor based on a command position for the first piston, wherein
the control device includes:
an observer that derives an estimated position of the first piston based on the position of the second piston detected by using the position sensor; and
a position controller that derives a target rotational speed of the motor based on a deviation between the estimated position of the first piston and the command position.

2. The hydraulic forceps system according to claim 1, wherein
the position sensor is a rotary encoder that detects a rotational displacement of the motor and converts the rotational displacement into the position of the second piston.

3. The hydraulic forceps system according to claim 2, further comprising a pressure sensor that detects a pressure of the hydraulic fluid, wherein
the observer derives the estimated position of the first piston based on the pressure of the hydraulic fluid detected by the pressure sensor and the position of the second piston detected by using the position sensor.

4. The hydraulic forceps system according to claim 3, wherein
the observer:
derives an estimated position of the second piston and an estimated pressure of the hydraulic fluid;
calculates an estimated error based on a deviation between the pressure of the hydraulic fluid detected by the pressure sensor and the estimated pressure of the hydraulic fluid and a deviation between the position of the second piston detected by using the position sensor and the estimated position of the second piston; and
feeds back the calculated estimated error to the deriving of the estimated position of the first piston.

5. The hydraulic forceps system according to claim 1, further comprising a pressure sensor that detects a pressure of the hydraulic fluid, wherein
the observer derives the estimated position of the first piston based on the pressure of the hydraulic fluid detected by the pressure sensor and the position of the second piston detected by using the position sensor.

6. The hydraulic forceps system according to claim 5, wherein
the observer:
derives an estimated position of the second piston and an estimated pressure of the hydraulic fluid;
calculates an estimated error based on a deviation between the pressure of the hydraulic fluid detected by the pressure sensor and the estimated pressure of the hydraulic fluid and a deviation between the position of the second piston detected by using the position sensor and the estimated position of the second piston; and
feeds back the calculated estimated error to the deriving of the estimated position of the first piston.

* * * * *